United States Patent [19]

Geuss

[11] 4,374,281
[45] Feb. 15, 1983

[54] PROCESS FOR THE MANUFACTURE OF HYDROQUINONE-MONOPHENYL ETHERS

[75] Inventor: Reinhart Geuss, Frankfurt am Main, Fed. Rep. of Germany

[73] Assignee: Hoechst Aktiengesellschaft, Frankfurt am Main, Fed. Rep. of Germany

[21] Appl. No.: 261,794

[22] Filed: May 8, 1981

[30] Foreign Application Priority Data

May 10, 1980 [DE] Fed. Rep. of Germany ....... 3018004

[51] Int. Cl.³ .............................................. C07C 41/16
[52] U.S. Cl. .................................................. 568/637
[58] Field of Search .......................................... 568/637

[56] References Cited

U.S. PATENT DOCUMENTS 3,966,826  6/1976  Trosken ............................. 568/637

Primary Examiner—Bernard Helfin
Attorney, Agent, or Firm—Curtis, Morris & Safford

[57] ABSTRACT

Hydroquinone-monophenyl ethers and their alkali metal salts of the formula

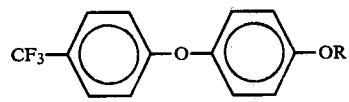

I (R=H or alkali) are obtained by reacting compounds of the formula

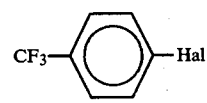

II with an excess of a compound of the formula

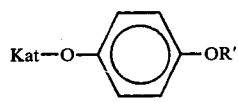

III (Kat=Na, K) in N-methylpyrrolidone at 230°–260° C.

2 Claims, No Drawings

PROCESS FOR THE MANUFACTURE OF HYDROQUINONE-MONOPHENYL ETHERS

Hydroquinone-monophenyl ethers of the formula

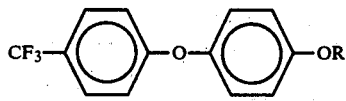

I in which R is hydrogen or a monovalent cation are valuable starting compounds for the manufacture of selective grass herbicides (see German Offenlegungsschrift No. 2,433,067 which corresponds to U.S. application Ser. No. 594,031, filed July 8, 1975). According to the cited Offenlegungsschrift, they are obtained by reacting in known manner halogen compounds of the formula

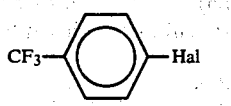

II in which Hal is halogen, with hydroquinone derivatives of the formula

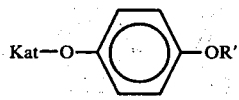

III in which Kat is a monovalent cation and R' is R or $(C_1-C_4)$-alkyl.

The reaction is carried out in a polar aprotic solvent at a reaction temperature of from 120° to 200° C., preferably around 170° C. In case R' is $(C_1-C_4)$-alkyl the alkyl group in the reaction product is eliminated by ether splitting.

An essential disadvantage of the above process resides in the fact that in the case where R or R' is a monovalent cation, the final product I continues to react partially with still unreacted II to give the hydroquinonebis-phenyl ether IV (bis-ether):

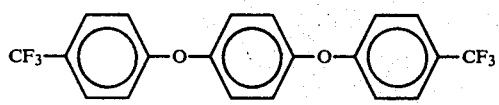

IV which not only reduces the yield of I but requires an expensive work-up process for I.

U.S. Pat. No. 4,172,959 describes that bis-ethers of the formula IV can be split by reaction with hydroquinone derivatives of the formula III at temperatures of from 120° to 200° C. (preferably also 170° C.) to give hydroquinone-monophenyl ethers. In the reaction of II with III (R'=R), therefore, two reactions which determine the content of the bis-ether IV in the reaction mixture compete with each other:

(a) I (R=monovalent cation) reacts with still unreacted II (reaction forming IV)
(b) IV reacts with unreacted III (R'=R) (reaction splitting IV).

For reasons of economy it is essential to keep the bis-ether content in the reaction mixture at such a low level that its separation and work-up according to U.S. Pat. No. 4,172,959 can be dispensed with. The limit is about 1%.

This requirement, however, cannot be met under the conditions of the state of the art.

For instance, the reaction of III (R'=R) with II in dimethyl sulfoxide (DMSO) according to U.S. Pat. No. 3,966,826 after 4 hours at 170° C. yields the final product I, but the distillation residue still contains 16% of bis-ether.

Similarly, splitting of the bis-ether by means of hydroquinone-dipotassium salt in DMSO after 8 hours at 170° C. according to U.S. Pat. No. 4,172,959 yields only 67% of the hydroquinone-monophenyl ether I. As has been found in further tests, the yield of 4-trifluoromethyl-4'-hydroxydiphenyl ether (I) can be increased to about 85–88% and the bis-ether content decreased accordingly to 4% when using an excess of about 15% of hydroquinone-dipotassium salt (DMSO, 8 hours at 170° C.) according to Germen Offenlegungsschrift No. 2,433,066; further heating, however, causes heavy decomposition of the reaction mixture before the bis-ether is split further.

When using other solvents such as indicated in the above German Offenlegungsschrift decomposition is prevented, but the reaction speed is substantially reduced and the bis-ether amount is increased. When operating at 180° C. in N-methyl pyrrolidone (excess of hydroquinone-dipotassium salt as above) the total yield (4-trifluoromethyl-4'-hydroxydiphenyl ether plus bis-ether) reaches a final 92% after 7 hours of which no less than 21% are bis-ether.

Surprisingly, it has now been found that when applying higher temperatures (230° to 260° C.) while maintaining all other conditions as indicated above the amount of bis-ether in the reaction mixture can be decreased to less than 1% with simultaneous increase of the yield of I by more than 20%.

Subject of the invention is therefore a process for manufacture of hydroquinone-monophenyl ethers of the formula

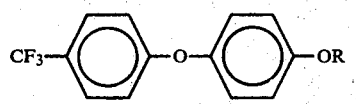

I in which R is hydrogen or an alkali metal cation, which comprises reacting halogen compounds of the formula

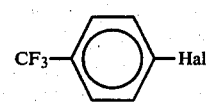

II with an at least 10% excess of a hydroquinone derivative of the formula

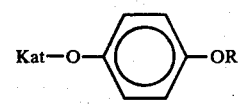

V in N-methyl pyrrolidone at a temperature of from 230° to 260° C.

The excess of V is preferably 15–18%. Although an excess of more than 20% may be used, it means increased consumption of starting material and is therefore not recommended.

The reaction time is from about 2 to 10 hours. Longer reaction time, an excess of below 10% and a temperature higher than 260° C. result in an increase of bis-ether content in the reaction product.

The reaction is advantageously carried out as follows:

First, the starting compound V is prepared from hydroquinone and an alkali metal hydroxide or corresponding alcoholate in N-methyl pyrrolidone. Per mol of hydroquinone about 1.7 to 2.0 mols of base (for example KOH, NaOH, sodium or potassium methylate or ethylate) are used, a further excess being not advantageous. Alcohol or water formed in this process must be removed in usual manner, e.g. by distillation before further reaction with II.

The amount of solvent is generally between 5 and 10 parts by weight per part of compound V. The compound II can be added under pressure at reaction temperature. However, it is easier to add II below the boiling point of N-methyl pyrrolidone (202° C.), i.e. without pressure. Advantageously, the temperature is chosen at such a level (160°–190° C.) that V is rapidly converted to I or IV without causing a too heavy reflux of II. Subsequently, the reaction vessel is closed and the batch is heated to reaction temperature.

For work-up of the reaction mixture, the solvent is substantially distilled off, the residue is introduced into water and acidified, and the hydroquinone-monophenyl ether is extracted from the aqueous phase by means of a suitable solvent. The crude product remaining after evaporation of the solvent can be directly reacted further according to German Offenlegungsschrift No. 2,433,067.

The following examples illustrate the invention without limiting it thereto.

EXAMPLE 1

From a solution of 4.8 kg (43.6 mols) of hydroquinone in 60.0 kg of N-methyl pyrrolidone and 10.0 kg (89.3 mols) of 50% aqueous potassium hydroxide solution a mixture of N-methyl pyrrolidone/water is distilled off under exclusion of oxygen until the water content in the distillate is below 1%.

6.8 kg (37.7 mols) of p-chlorobenzotrifluoride are added within 1.5 hours at 175° C. to the suspension formed, the reaction vessel is then closed and rapidly heated to 255° C. The pressure is about 2–3 bar during this operation. After 3 hours at 255° C., the batch is allowed to cool, and the solvent is substantially distilled off at 4 mbar. The distillation residue is introduced into 20 kg of water, acidified with concentrated hydrochloric acid, and the aqueous phase is extracted with octane. After evaporation of the octane, 10.4 kg of crude product are obtained which contains according to an analysis 12.3% of N-methyl pyrrolidone, 86.4% of 4-trifluoromethyl-4'-hydroxydiphenyl ether (corresponding to 93.7% of theory) and 0.5% of hydroquinone-bis-(4-trifluoromethyl)-phenyl ether. If required, the crude product can be purified by distillation.

EXAMPLE 2

When heating the reaction mixture for 6 hours at 235° C., work-up yields 10.3 kg of crude product containing 13.0% of N-methyl pyrrolidone, 85.3% of 4-trifluoromethyl-4'-hydroxydiphenyl ether (corresponding to 91.5% of theory) and 0.8% of hydroquinone-bis-(4-trifluoromethyl)-phenyl ether.

EXAMPLE 3

When using 6.3 kg (90.0 mols) of potassium methylate instead of 50% aqueous potassium hydroxide solution and subsequently distilling off methanol, 10.1 kg of crude product containing 12.5% of N-methyl pyrrolidone, 84.7% of 4-trifluoromethyl-4'-hydroxydiphenyl ether (corresponding to 89.3% of theory) and 0.6% of hydroquinonebis-(4-trifluoromethyl)-phenyl ether are obtained.

What is claimed is:

1. In a process for the manufacture of hydroquinone-monophenyl ethers of their alkali metal salts of the formula

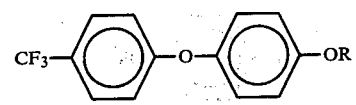

I in which R is hydrogen or an alkali metal cation by reacting halogen compounds of the formula

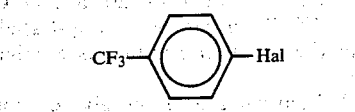

II in which Hal is chlorine or bromine, with a hydroquinone derivative of the formula

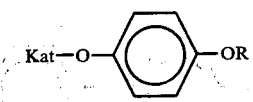

V in which Kat is sodium or potassium, in N-methyl pyrrolidone, the improvement which comprises carrying out the reaction at a temperature of from 230° to 260° C. and with an at least 15% excess of hydroquinone derivative.

2. The process as claimed in claim 1, wherein the excess of V relative to II is 15–18%.

* * * * *